United States Patent [19]

Naito et al.

[11] Patent Number: 5,068,399

[45] Date of Patent: Nov. 26, 1991

[54] PROCESS FOR PREPARING UNSATURATED CARBOXYLIC ACID ESTER

[75] Inventors: Susumu Naito; Takao Kouzai; Ritoko Ikeda, all of Niigata, Japan

[73] Assignee: Mitsubishi Gas Chemical Company, Inc., Tokyo, Japan

[21] Appl. No.: 583,802

[22] Filed: Sep. 17, 1990

[30] Foreign Application Priority Data

Nov. 28, 1989 [JP] Japan .................................. 1-306647

[51] Int. Cl.$^5$ ............................................ C07C 67/317
[52] U.S. Cl. ..................................... 560/212; 560/205; 560/211; 560/214; 562/599
[58] Field of Search ............... 560/183, 205, 211, 212, 560/214; 562/599

[56] References Cited

U.S. PATENT DOCUMENTS

| | | | |
|---|---|---|---|
| 3,487,101 | 12/1969 | Volker et al. | 560/205 |
| 4,833,267 | 5/1989 | Nakashima et al. | 560/205 |
| 4,933,487 | 6/1990 | Hoelderich et al. | 560/205 |

*Primary Examiner*—Jose G. Dees
*Assistant Examiner*—Vera C. Clarke
*Attorney, Agent, or Firm*—Frishauf, Holtz, Goodman & Woodward

[57] ABSTRACT

Disclosed is a process for preparing, $\alpha$, $\beta$-unsaturated carboxylic acid ester from $\alpha$-hydroxycarboxylic acid ester, a $\alpha$-alkoxycarboxylic acid ester or $\beta$-alkoxycarboxylic acid ester as a starting material by a vapor-phase catalytic reaction in the presence of a crystalline aluminosilicate modified with an alkali metal and a platinum group element as a catalyst.

According to the process, $\alpha$, $\beta$-unsaturated carboxylic acid can be produced efficiently.

26 Claims, No Drawings

PROCESS FOR PREPARING UNSATURATED CARBOXYLIC ACID ESTER

BACKGROUND OF THE INVENTION

1. Field of the Invention

This invention relates to a process for preparing industrially an α, β-unsaturated carboxylic acid ester using at least one acid ester selected from an α-hydroxycarboxylic acid ester, an α-alkoxycarboxylic acid ester, and a β-alkoxycarboxylic acid ester as starting materials.

2. Description of the Related Arts

The α, β-unsaturated carboxylic acid ester is very useful in industry as a starting material for synthetic resins. In particular, methyl methacrylate obtained from methyl α-hydroxyisobutyrate, methyl α-methoxyisobutyrate or methyl β-methoxyisobutyrate have been important for practical use because methyl methacrylate can be used as a starting material for polymethyl methacrylate having excellent weather resistance and transparency.

As for a process of preparing α, β-unsaturated carboxylic acid or its ester, a process in which a dehydrating reaction of an α-hydroxycarboxylic acid ester is carried out in a liquid phase, has heretofore been disclosed in, for example, U.S. Pat. No. 3,487,101.

In addition, in Japanese Patent Publication No. 184047/1985, a process is disclosed in which methyl methacrylate is prepared by reacting concentrated sulfuric acid having a concentration of 90 to 100% with methyl α-hydroxyisobutyrate in a liquid phase.

However, in the process for preparing methacrylic acid ester using sulfuric acid, there are great difficulties in practical application at an industrial scale because an extremely excess amount of highly concentrated sulfuric acid is required and the problem of processing a large amount of waste sulfuric acid diluted with water formed by the reaction is involved.

On the other hand, a process has been proposed for preparing methyl methacrylate from methyl α-hydroxyisobutyrate by a vapor phase catalytic reaction using a solid catalyst such as phosphate.

For example, in Japanese Patent Publication No. 20611/1969, No. 20612/1969 and No. 15724/1970, there are disclosed processes in which high boiling point materials such as methyl α-hydroxyisobutyrate, methyl α-methoxyisobutyrate and methyl β-methoxyisobutyrate among the impurities contained in crude methyl methacrylate synthesized by the acetone cyanohydrin method, are passed through a catalytic layer wherein solid phosphoric acid, alkali metal salts of phosphoric acid, or alkaline earth metal salts of phosphoric acid deposited on silica or silica-alumina to obtain methyl methacrylate and methacrylic acid.

However, when these phosphate catalysts are used, a high reaction temperature is required so that deposition of a large amount of carbonaceous material and a side reaction such as a hydrogenation reaction occur causing problems in that, for example, methyl isobutyrate is formed as a by-product in a large amount, and therefore the above described processes cannot be satisfactory for practical use.

SUMMARY OF THE INVENTION

In view of the prior art problems, the present inventors have studied a process for production of methyl methacrylate by a gas-phase catalytic reaction of methyl α-hydroxyisobutyrate, for example, using X or Y type zeolite. As a result of intensive studies to improve the above zeolite, a catalyst, which permits to minimize by-production of ether and which has high activity and a long catalytic life time, has been disclosed. The present invention has been established on the basis of these knowledge.

That is, the present invention provides a process for preparing α, β-unsaturated carboxylic acid ester which comprises catalytically reacting at least one compound selected from α-hydroxycarboxylic acid ester, α-alkoxycarboxylic acid ester and β-alkoxycarboxylic acid ester in a vapor phase in the presence of a catalyst consisting essentially of crystalline aluminosilicate modified with an alkali metal and a platinum group element.

DESCRIPTION OF THE PREFERRED EMBODIMENTS

In the following, the process of the present invention is described in more detail.

The process of the present invention is characterized by using X-type or Y-type zeolites modified with an alkali metal and a platinum group element.

The X-type or the Y-type zeolite mentioned herein includes synthetic zeolite, and for example, when it is NaX type or NaY type zeolite, it is represented by the following formula:

NaX type:

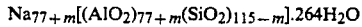

$(0 < m < 17)$

NaY type:

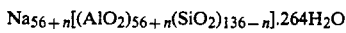

$(-8 < n < 20)$.

These zeolites include commercially available zeolite such as Molecular Sieve 13X (trade mark).

Alkali metals and platinum group elements to be used in modification of X-type or Y-type zeolite in the process of the present invention are Li, Na, K, Cs, Rb, etc. as selected from Group Ia of the Periodic Table, and Pt, Pd, Rh, Ru, etc. selected from Group VIIIb of the Periodic Table.

In connection with the amounts of the alkali metal and the platinum metal element used in the modification of the zeolite, the former is not more than 30% by weight and preferably 1 to 15% by weight, and the latter is not more than 5% by weight and preferably 0.1 to 1% by weight.

For the modification with each element, there is employed a method in which a compound containing each element is used and the zeolite is impregnated or kneaded with the compound as such or in the state that it is dissolved in a solvent. That is, the desired product is prepared by a method in which the zeolite is used as a support, or a method in which part of Na ions in the zeolite is ion-exchanged.

The order of modification with each element is not critical. It is, however, preferred that the zeolite should be modified with the alkali metal and then with the platinum metal element.

The catalyst thus prepared is dried at 100° to 150° C., and then calcined at not more than 600° C. and preferably 300° to 500° C. In some cases, the catalyst can be used after reduction with hydrogen, for example, at not more than 600° C.

The reaction using at least one compound selected from α-hydroxycarboxylic acid ester, α-alkoxycarboxylic acid ester and β-alkoxycarboxylic acid ester as starting materials in the presence of the catalyst can be carried out in the absence of a solvent, or in the presence of a solvent. When the reaction is carried out in the presence of a solvent, α, β-unsaturated carboxylic acid ester can be obtained with high selectivity. That is, the selectivity of α, β-unsaturated carboxylic acid ester can be increased by using an alcohol corresponding to the alkoxyl portion of the ester as a solvent.

In the process of the present invention, if methyl α-hydroxyisobutyrate is used as a starting material, and methanol is used as a solvent, methyl methacrylate containing almost no impurities such as dimethyl ether and methyl isobutyrate is synthesized. Accordingly, a product of methyl methacrylate with high purity can be easily obtained by applying conventional easy operations such as extraction and distillation onto the above reaction product.

The process of the present invention can be performed as shown below.

Into a tubular reactor with corrosion resistance is charged a predetermined amount of a modified crystalline aluminosilicate catalyst, and if necessary, a small amount of nitrogen is passed through it as a carrier gas, and a solution of at least one compound of α-hydroxycarboxylic acid ester, α-alkoxycarboxylic acid ester and β-alkoxycarboxylic acid ester as starting materials with a concentration of 10 to 100%, preferably 30 to 85% was supplied thereto continuously at a reaction temperature in the range of 150° to 450° C., preferably 200° to 350° C.

When a solvent is used in the reaction, an alcohol corresponding to the alkoxyl portion of the α, β-unsaturated carboxylic acid ester is preferably used.

In the process of the present invention, the reaction can be carried out in a vapor phase catalytic reaction, but it is preferably carried out in a vapor phase reaction using a fixed bed. The starting material in a liquid state is also preferably preliminarily heated and then supplied to the reactor in a vapor state.

When the methyl α-hydroxyiosbutyrate, methyl α-methoxyisobutyrate or methyl β-methoxyisobutyrate is used as starting material, a small amount of unreacted starting material or by-products such as acetone and ether is contained in a reaction product, in addition to the objective methyl methacrylate and methacrylic acid. However, if an extraction method or a distillation method is applied to the reaction product, a product of methyl methacrylate with a high purity can be easily obtained. In addition, the unreacted starting material recovered by this operation can be utilized again in the reaction.

In accordance with the process of the present invention, α, β-unsaturated carboxylic acid ester can be produced at low production costs under mild conditions and in high yields while minimizing by-production of ether by using α-hydroxycarboxylic acid ester, α-alkoxycarboxylic acid ester or β-alkoxycarboxylic acid ester as starting material, and crystalline aluminosilicate modified with an alkali metal and a platinum metal element as a catalyst. Thus the process of the present invention is of high industrial significance.

The present invention is described in greater detail with reference to the following examples, although it is not intended to be limited thereto.

EXAMPLE 1

Thirty grams of Molecular Sieve 13X was soaked overnight in an aqueous solution of cesium acetate, and then dried under reduced pressure and calcined at 500° C. for 3 hours in an electric furnace to deposit 10% of cesium thereon. Subsequently, the molecular sieve was soaked overnight in an ethanol solution of ruthenium chloride, and then dried under reduced pressure and calcined at 500° C. for 3 hours to deposit 0.5% of ruthenium thereon. In this way, the desired catalyst was prepared.

In a tubular reactor made of a quartz having an inner diameter of 15 mm and a length of 450 mm was packed 5 grams of the above modified Molecular Sieve 13X as a catalyst, and the temperature of the catalyst layer was maintained at 260° C.

Four grams per hour (g/hr) of methyl α-hydroxyisobutyrate with a concentration of 50% dissolved in methanol as a solvent was vaporized through a preheating layer and supplied into the catalyst layer.

The solution produced was analyzed to obtain the results that a conversion of methyl α-hydroxyisobutyrate was 99%, a selectivity into methyl methacrylate was 94.6%, a selectivity into methacrylic acid was 2%, and selectivities into acetone and methyl α-methoxyisobutyrate were each less than 1%.

The conversion of the methanol solvent into a dimethyl ether as by-product was 0.5%, and the recovery of the methanol solvent was 99.2%.

The yield of methyl methacrylate after the reaction at 260° C. for 300 hours was 90.2%.

EXAMPLE 2

Thirty grams of Molecular Sieve 13X was soaked in an aqueous solution of potassium hydroxide, dried under reduced pressure, and then calcined at 500° C. for 3 hours to deposit 10% of potassium thereon. Subsequently, the molecular sieve was soaked overnight in an aqueous solution of chloroplatinic acid, dried under reduced pressure, and calcined at 500° C. for 3 hours to deposit 0.5% of platinum thereon. In this manner, a catalyst with 10% of potassium and 0.5% of platinum deposited on Molecular Sieve 13X was obtained.

A tubular reactor (inner diameter 15 mm, length 450 mm) made of quartz glass was charged with 5 grams of the above modified Molecular Sieve 13X as a catalyst, and the temperature of a catalyst layer was maintained at 260° C.

A 50% concentration methanol solution of methyl α-hydroxyisobutyrate was vaporized by passing through a preheating layer and introduced into the catalyst layer at a rate of 4 g/hr.

An analysis of the product showed that the conversion of methyl α-hydroxyisobutyrate was 99%, the selectivity into methyl methacrylate was 93%, the selectivity into methacrylic acid was 2.7%, and the selectivities into acetone and methyl α-methoxyisobutyrate were each less than 1%.

The conversion of the methanol solvent into the dimethyl ether as by-product was 0.5%, and the recovery of the methanol solvent was 99.3%.

The yield of methyl methacrylate after the reaction at 260° C. for 300 hours was 87.7%.

EXAMPLE 3

The reaction was carried out in the same manner as in Example 1 except that a mixture of equal amounts of methyl α-methoxyisobutyrate and methyl β-methoxyisobutyrate was used in place of methyl α-hydroxyisobutyrate.

An analysis of the product showed that the conversion of methyl α, β-hydroxyisobutyrate was 99%, the selectivity into methyl methacrylate was 94.2%, the selectivity into methacrylic acid was 2.1%, and the selectivities into acetone and methyl α-methoxyisobutyrate were each less than 1%.

The conversion of the methanol solvent into the dimethyl ether as by-product was 0.6%, and the recovery of the methanol solvent was 99.2%.

The yield of methyl methacrylate after the reaction at 260° C. for 300 hours was 89.7%.

EXAMPLE 4

The reaction was carried out in the same manner as in Example 1 except that methyl lactate was used in place of methyl α-hydroxyisobutyrate.

An analysis of the product showed that the conversion of methyl lactate was 99%, the selectivity into methyl acrylate was 93.2%, the selectivity into acrylic acid was 2.1%, and the selectivities into acetoaldehyde and methyl α-methoxypropionate were each less than 1%.

The conversion of the methanol solvent into the dimethyl ether as by-product was 0.9%, and the recovery of the methanol solvent was 98.6%.

The yield of methyl acrylate after the reaction at 260° C. for 300 hours was 90.3%.

COMPARATIVE EXAMPLE 1

Thirty grams of Molecular Sieve 13X was soaked overnight in an aqueous solution of cesium acetate, dried under reduced pressure, and calcined in an electric furnace at 500° C. for 3 hours to obtain a catalyst with 10% of cesium deposited thereon.

A tubular reactor (inner diameter 15 mm, length 450 mm) made of quartz glass was charged with 5 grams of the above modified Molecular Sieve 13X as a catalyst, and the temperature of a catalyst layer was maintained at 260° C.

A 50% concentration methanol solution of methyl α-hydroxyisobutyrate was vaporized by passing through a preheating layer and introduced into the catalyst layer at a rate of 4 g/hr.

An analysis of the product showed that the conversion of methyl α-hydroxyisobutyrate was 99%, the selectivity into methyl methacrylate was 94.4%, the selectivity into methacrylic acid was 2.1%, and the selectivities into acetone and methyl α-methoxyisobutyrate were each less than 1%.

The conversion of the methanol solvent into the dimethyl ether as by-product was 0.8%, and the recovery of the methanol solvent was 99.2%.

The yield of methyl methacrylate after the reaction a 260° C. for 300 hours was 48%.

COMPARATIVE EXAMPLE 2

The reaction was carried out in the same manner as in Example 1 except that 5 grams of Molecular Sieve 13X subjected to no modification was used as a catalyst.

An analysis of the product showed that the conversion of methyl α-hydroxyisobutyrate was 99%, the selectivity into methyl methacrylate was 93%, the selectivity into methacrylic acid was 2%, and the selectivities into acetone and methyl α-methoxyisobutyrate were each less than 1%.

The conversion of the methanol solvent into the dimethyl ether as by-product was 9.8%, and the recovery of the methanol solvent was 88.2%.

The yield of methyl methacrylate after the reaction at 260° C. for 300 hours was 50.6%.

What is claimed is:

1. A process for preparing α, β-unsaturated carboxylic acid ester which comprises catalytically reacting at least one acid ester compound selected from the group consisting of an α-hydroxycarboxylic acid ester selected from the group consisting of methyl α-hydroxyisobutyrate and methyl lactate, an α-alkoxycarboxylic acid ester selected from the group consisting of methyl α-methoxyisobutyrate and methyl α-methoxypropionate and aβ-alkoxycarboxylic acid ester selected from the group consisting of methyl β-methoxyisobutyrate and methyl β-methoxypropionate, in a vapor phase in the presence of a catalyst consisting essentially of crystalline aluminosilicate modified with an alkali metal and a platinum group element.

2. The process as defined in claim 1 wherein the crystalline aluminosilicate is X type zeolite.

3. The process as defined in claim 1 wherein the crystalline aluminosilicate is Y type zeolite.

4. The process as defined in claim 2 wherein the X type zeolite is Molecular Sieve 13X.

5. The process as defined in claim 1 wherein the alkali metal is Li, Na, K, Cs, or Rb.

6. The process as defined in claim 1 wherein the platinum group element is Pt, Pd, Rh, Ru, Ir, or Os.

7. The process as defined in claim 1 which further comprises conducting the reaction in the presence of a diluent, said diluent being an alcohol corresponding to the alkoxyl portion of the ester.

8. The process as defined in claim 5, wherein the platinum group element is Pt, Pd, Rh, Ru, Ir, or Os.

9. The process as defined in claim 8, wherein the crystalline aluminosilicate is X type zeolite.

10. The process as defined in claim 9, wherein the X type zeolite is Molecular Sieve 13X.

11. The process as defined in claim 8, wherein the crystalline aluminosilicate is Y type zeolite.

12. The process as defined in claim 9, wherein the X type zeolite is NaX type zeolite.

13. The process as defined in claim 11, wherein the Y type zeolite is NaY type zeolite.

14. The process as defined in claim 12, wherein the NaX type zeolite is of the formula $$Na_{77+m}((AlO_2)_{77+m}(SiO_2)_{115-m})-264H_2O$$

wherein $0 < m < 17$.

15. The process as defined in claim 13, wherein the NaY type zeolite is of the formula $$Na_{56+m}((AlO_2)_{56+m}(SiO_2)_{136-m})-264H_2O$$

wherein $-8 < n < 20$.

16. The process as defined in claim 8, wherein the alkali metal is in an amount of not more than 30% by weight and the platinum group element is in an amount of not more than 5% by weight.

17. The process as defined in claim 8, wherein the alkali metal is in an amount of 1 to 15% by weight and the platinum group element is in an amount of 0.1 to 1% by weight.

18. The process as defined in claim 8, wherein the acid ester is in a concentration of 10 to 100%.

19. The process as defined in claim 8, wherein the acid ester is in a concentration of 30 to 85%.

20. The process as defined in claim 17, wherein the reaction is conducted at a temperature of 150° to 450° C.

21. The process as defined in claim 17, wherein the reaction is conducted at a temperature of 200° to 350° C.

22. The process as defined in claim 21, wherein the reaction is conducted in a fixed bed and the acid ester is in a concentration of 30 to 85%.

23. The process as defined in claim 7, wherein the crystalline aluminosilicate is Molecular Sieve 13X, the alkali metal is cesium, the platinum group element is ruthenium, the alcohol is ethanol and the acid ester is methyl α-hydroxyisobutyrate.

24. The process as defined in claim 7, wherein the crystalline aluminosilicate is Molecular Sieve 13X, the alkali metal is potassium, the platinum group element is platinum, the alcohol is methanol and the acid ester is methyl α-hydroxyisobutyrate.

25. The process as defined in claim 7, wherein the crystalline aluminosilicate is Molecular Sieve 13X, the alkali metal is cesium, the platinum group element is ruthenium, the alcohol is methanol and the acid ester comprises equal amounts of methyl α-methoxyisobutyrate and methyl β-methoxyisobutyrate.

26. The process as defined in claim 7, wherein the crystalline aluminosilicate is Molecular Sieve 13X, the alkali metal is cesium, the platinum group element is ruthenium, the alcohol is methanol and the acid is methyl lactate.

* * * * *